US012805957B2

(12) United States Patent
Lau et al.

(10) Patent No.: US 12,805,957 B2
(45) Date of Patent: Nov. 24, 2026

(54) ADAPTOR FOR USE WITH ONE OR MORE ROBOTIC SYSTEMS

(71) Applicant: MULTI-SCALE MEDICAL ROBOTICS CENTER LIMITED, Hong Kong (CN)

(72) Inventors: Ka Chun Lau, Hong Kong (CN); Ka Hei Yu, Hong Kong (CN); Fung Flora Leung, Hong Kong (CN); Ming Ho Ho, Hong Kong (CN); Yeung Yam, Hong Kong (CN); Wai Yan Philip Chiu, Hong Kong (CN)

(73) Assignee: MULTI-SCALE MEDICAL ROBOTICS CENTER LIMITED, Hong Kong (CN)

( * ) Notice: Subject to any disclaimer, the term of this patent is extended or adjusted under 35 U.S.C. 154(b) by 0 days.

(21) Appl. No.: 19/120,768

(22) PCT Filed: Oct. 12, 2023

(86) PCT No.: PCT/IB2023/060260
§ 371 (c)(1),
(2) Date: Apr. 12, 2025

(87) PCT Pub. No.: WO2024/079671
PCT Pub. Date: Apr. 18, 2024

(65) Prior Publication Data

US 2026/0096865 A1 Apr. 9, 2026

Related U.S. Application Data

(60) Provisional application No. 63/415,629, filed on Oct. 12, 2022.

(51) Int. Cl.
*A61B 34/37* (2016.01)
*A61B 1/00* (2006.01)
(Continued)

(52) U.S. Cl.
CPC ........... *A61B 34/37* (2016.02); *B25J 15/0408* (2013.01); *A61B 1/0016* (2013.01); *A61B 2034/301* (2016.02)

(58) Field of Classification Search
CPC ...................................................... A61B 34/37
See application file for complete search history.

(56) References Cited

U.S. PATENT DOCUMENTS 6,322,567 B1 * 11/2001 Mittelstadt ............. A61B 34/70 606/130
8,992,542 B2 * 3/2015 Hagag ....................... A61F 2/36 606/130

(Continued)

*Primary Examiner* — Christian A Sevilla
(74) *Attorney, Agent, or Firm* — Kinect Law, PLLC

(57) ABSTRACT

This invention provides an adaptor for use with one or more robotic manipulators. In one embodiment, said adaptor comprises: a) a bowl (101) for attachment to a carrier system; b) an overtube (102) connected to said bowl (101), comprising at least one channel for insertion of said one or more robotic manipulators; c) a plurality of controls (118), each control (118) is adapted to control diameter of one of said at least one channel; wherein said at least one channel comprises two or more inlets (107) converging into a same channel; and each of said two or more inlets (107) is positioned on opposite sides on said bowl (101) or overtube (102).

20 Claims, 11 Drawing Sheets

(51) Int. Cl.
*A61B 34/30* (2016.01)
*B25J 15/04* (2006.01)

(56) References Cited

U.S. PATENT DOCUMENTS

| | | | | |
|---|---|---|---|---|
| 2004/0106916 | A1 * | 6/2004 | Quaid .................... | A61B 34/71<br>606/1 |
| 2006/0142657 | A1 * | 6/2006 | Quaid .................... | A61B 90/37<br>600/424 |
| 2007/0270685 | A1 * | 11/2007 | Kang ..................... | A61B 90/03<br>600/424 |

* cited by examiner

ADAPTOR FOR USE WITH ONE OR MORE ROBOTIC SYSTEMS

FIELD OF THE INVENTION

The present invention generally relates to devices for use with robotic systems, particularly adaptors.

BACKGROUND OF THE INVENTION

Gastric and colorectal cancers were commonly found around the world. They are also the top leading causes of cancer death worldwide. Practically, minimally invasive surgery is widely used to evaluate illnesses and injuries which does not need a large incision during surgery. Wherein, Endoscopic Submucosal Dissection (ESD) and Endoscopic Mucosal Resection (EMR) were well-developed to remove pre-malignant and early cancers in the GI tract. These procedures are performed with a flexible endoscope which allows the patient to recuperate faster with less pain.

Commonly used technologies in the related surgical platform including retraction and dissection to enhance the overall operation effectiveness and safety. The robotic manipulators for retraction and dissection are designed to be a standalone instrument, which the robotic manipulators and the endoscopic platform are separated. This induces some problems, including relative motion between these components, complex deployment procedure into patient's body, relying on expensive dual-channel endoscope.

Meanwhile, in the current development of the surgical robotic system, dual-channel endoscope is commonly used. On the one hand, one of the disadvantages of using dual-channel endoscope as the carrier of the robotic manipulators is that the distance is too far away from the camera view to the distal end of the manipulators. On the other hand, the view angle cannot be adjusted which may be blocked by the manipulators in some cases.

SUMMARY OF THE INVENTION

This invention provides an adaptor for use with one or more robotic manipulators. In one embodiment, said adaptor comprises: a) a bowl (101) for attachment to a carrier system; b) an overtube (102) connected to said bowl (101), comprising at least one channel for insertion of said one or more robotic manipulators; c) a plurality of controls (118), each control (118) is adapted to control diameter of one of said at least one channel; wherein said at least one channel comprises two or more inlets (107) converging into a same channel; and each of said two or more inlets (107) is positioned on opposite sides on said bowl (101) or overtube (102).

This invention also provides a method for using the adaptor of this invention for surgery. In one embodiment, said adaptor of this invention comprises an overtube (102) is detachable from the bowl (101), said method comprises the steps of: a) positioning said overtube (102) at a target location; b) inserting an endoscope or endoscopic camera (106) into one of said at least one channel from one of said two or more inlets (107); c) attaching said bowl (101) to a carrier system; and d) connecting said bowl (101) to said overtube (102).

BRIEF DESCRIPTION OF THE FIGURES

Exemplary non-limiting embodiments of the invention are described below with reference to the attached drawings.

The drawings are illustrative and generally not to an exact scale. The same or similar elements on different figures are referenced with the same reference numbers.

FIGS. 2A and 2B show an embodiment of the all-in-one adaptor for flexible robotic manipulator deployed on a tailor-made multi-degree-of-freedom series type robotic arm.

FIGS. 2C and 2D show an embodiment of the all-in-one adaptor for flexible robotic manipulator deployed on a medical certificated robotic arm in different configurations for avoiding collisions with environmental and operators.

FIG. 2E shows an embodiment of the all-in-one adaptor for flexible robotic manipulator deployed on a ceiling movable arm using in the operation theatre.

DETAILED DESCRIPTION OF THE INVENTION

Figure 1A:
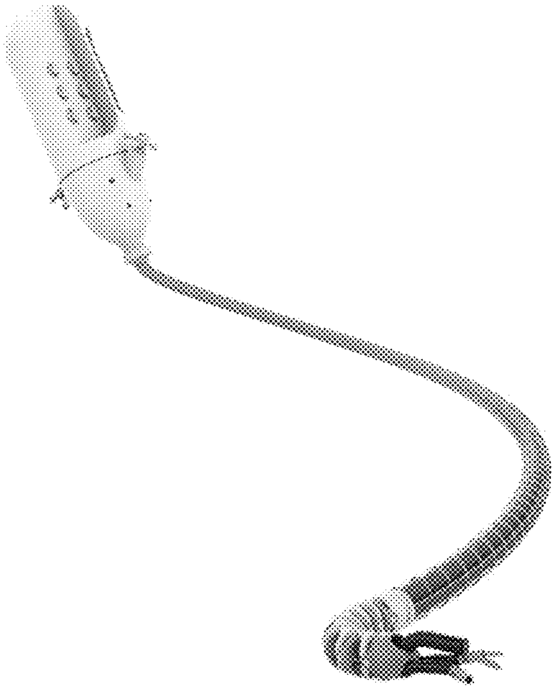
FIGS. 1A and 1B show an embodiment of the all-in-one adaptor for flexible robotic manipulator using in the surgical robotic platform in different views.
Figure 1B:
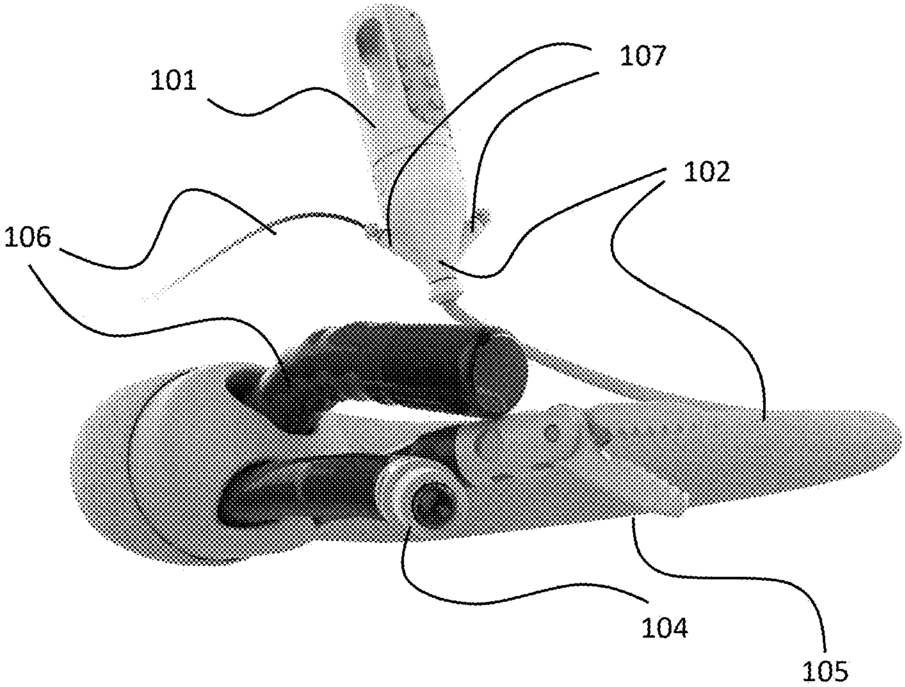
Figure 2A:
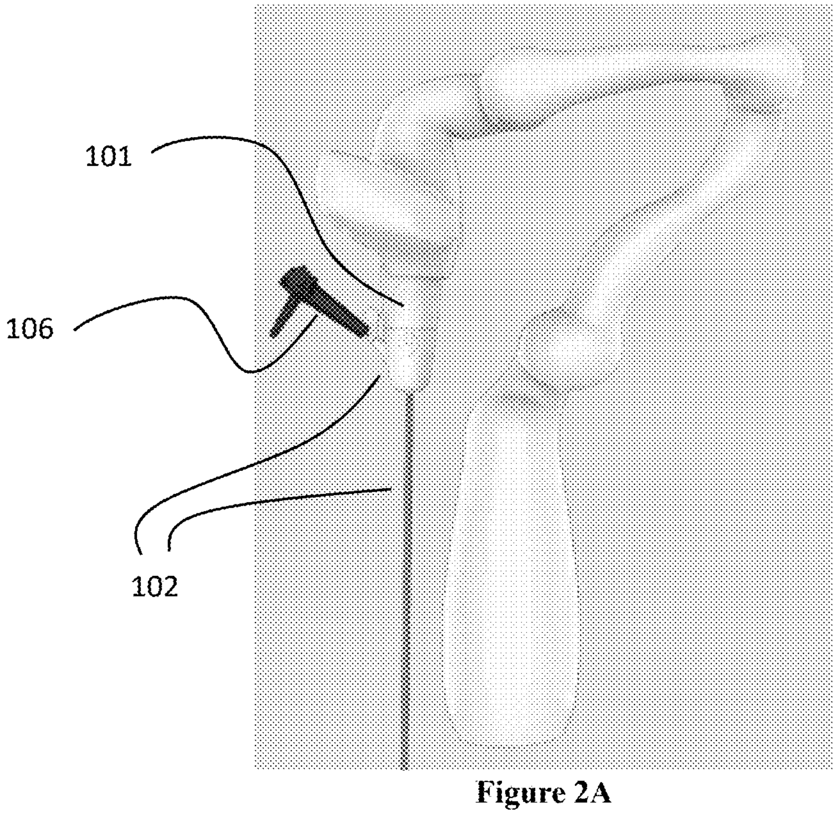
FIG. 2A to 2E show various embodiments of the carrier system for deploying flexible robotic manipulator of surgical robotic platform.
Figure 2B:
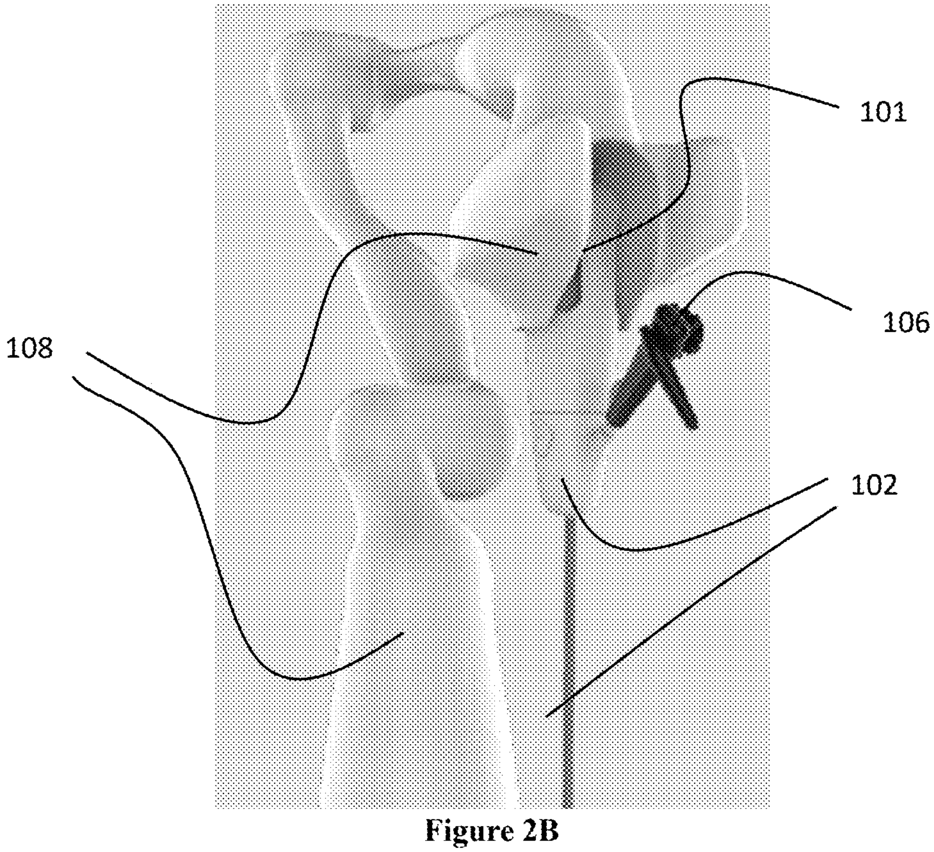
Figure 2C:
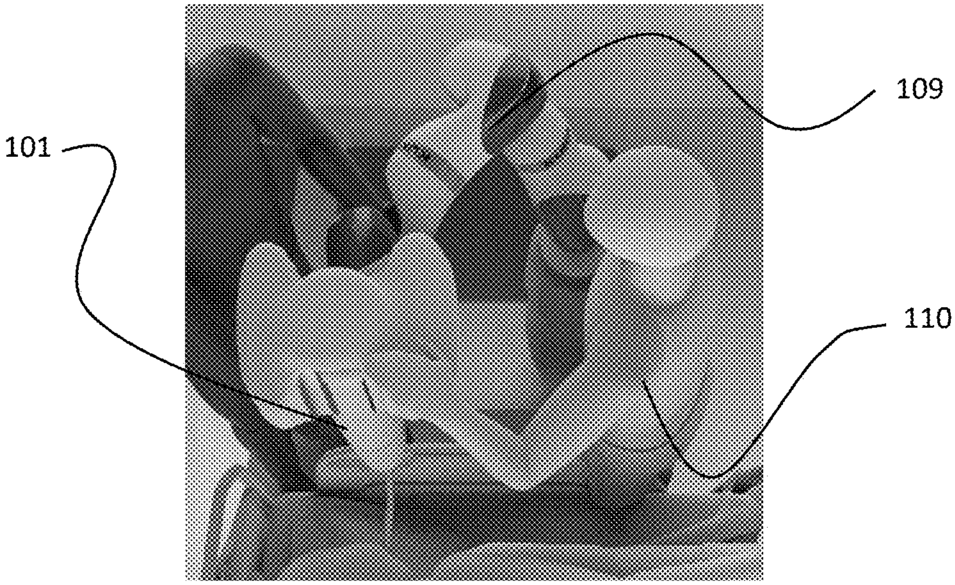
Figure 2D:
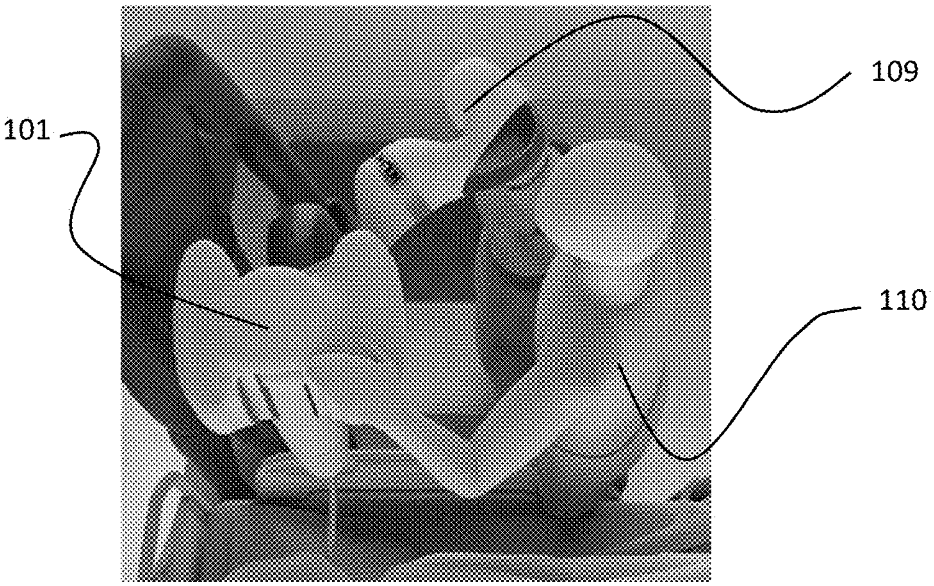
Figure 2E:
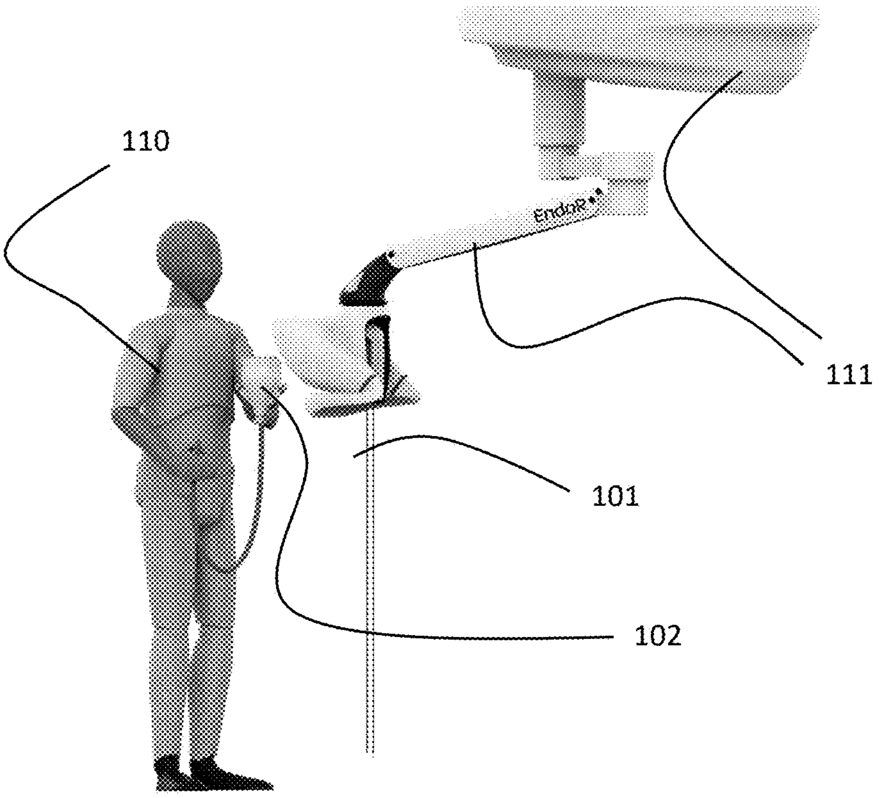
Figure 3A:
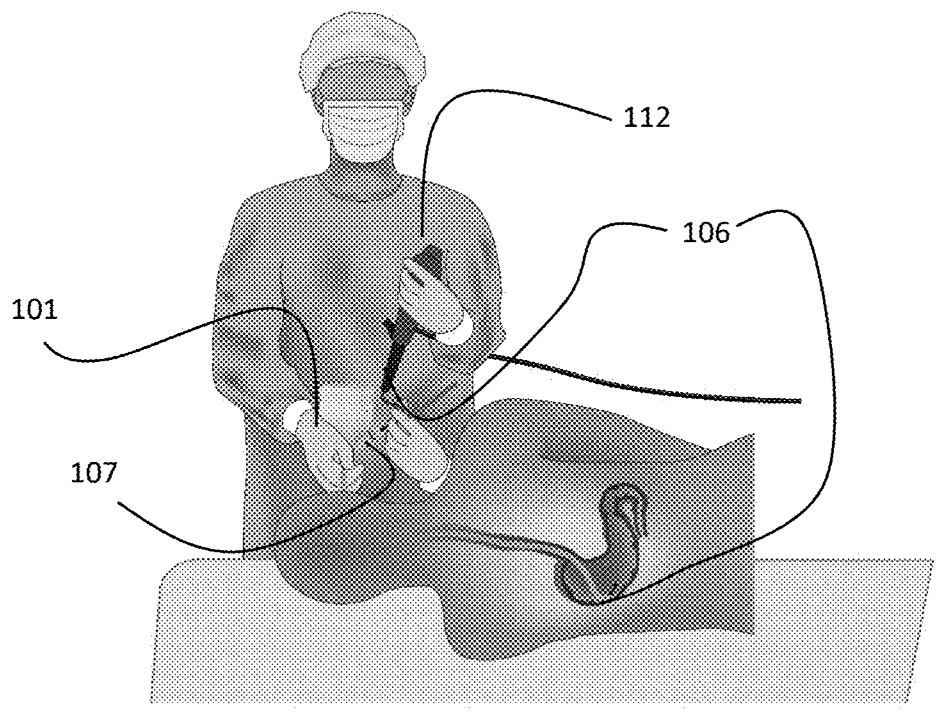
FIGS. 3A to 3C show various scenario of the deploying the endoscope or endoscopic camera for positioning of the endoscopic overtube.
Figure 3B:
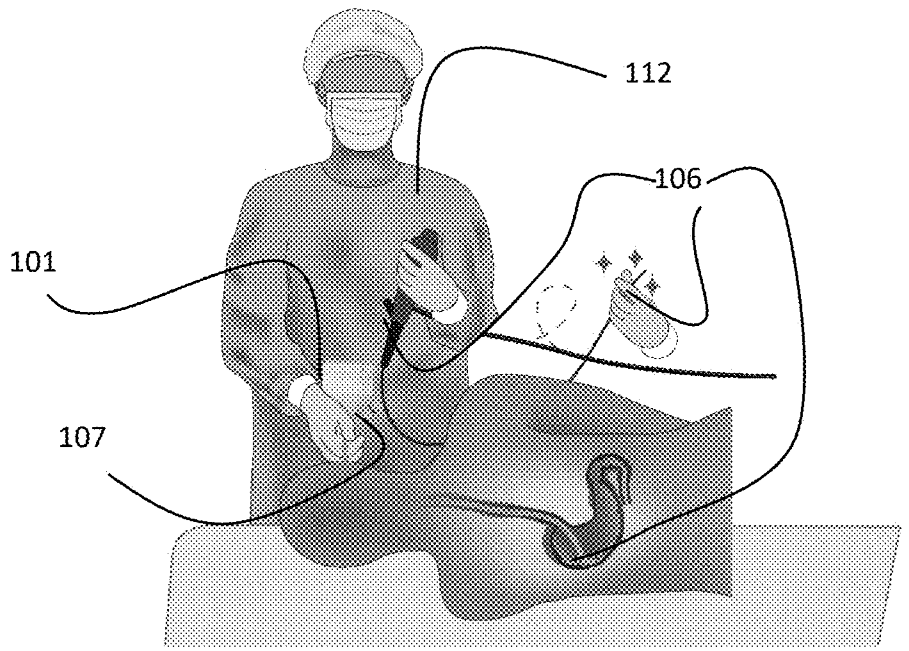
Figure 3C:
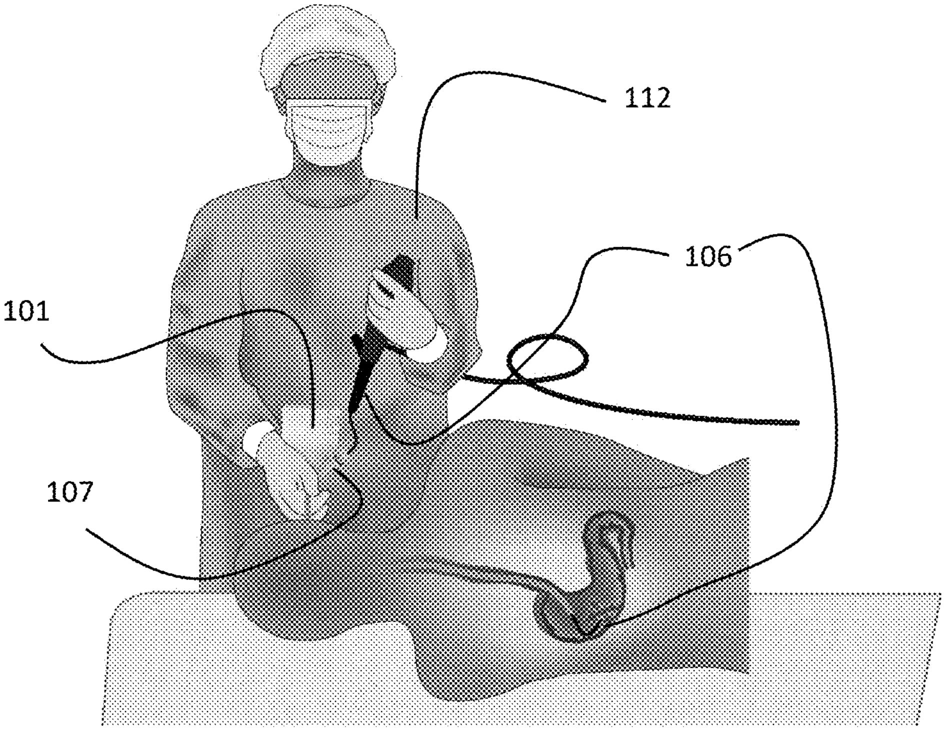
Figure 4:
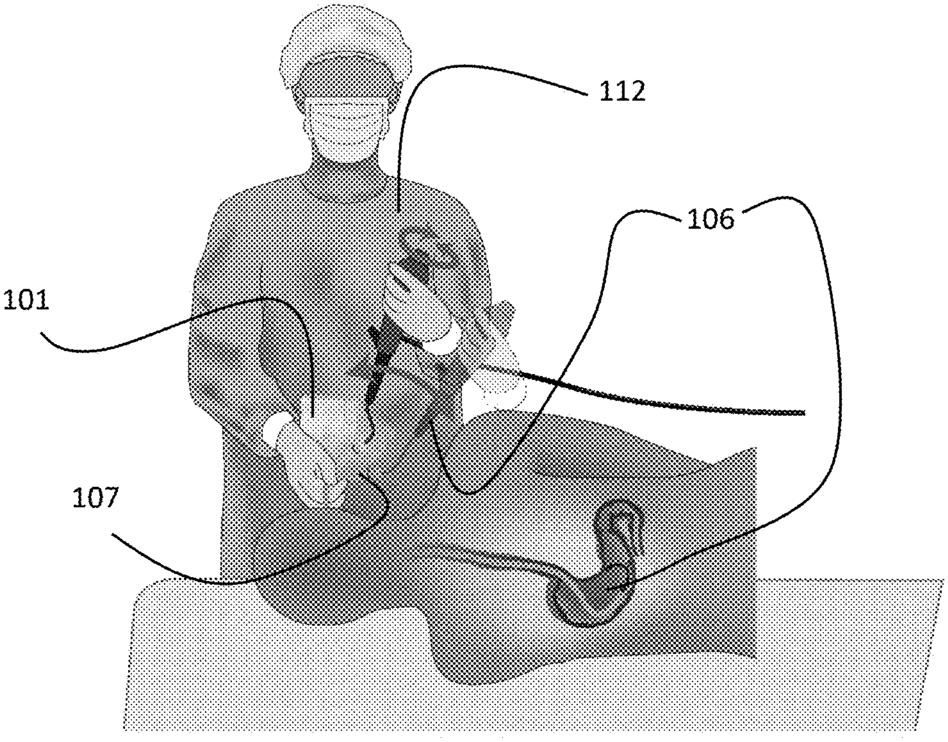
FIG. 4 shows the manipulation of the endoscopic overtube by the surgeon with all degree-of-freedom.
Figure 5A:
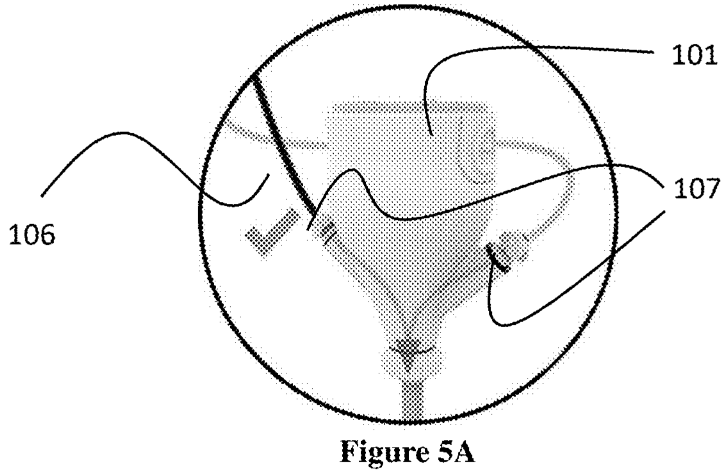
FIG. 5A shows the channel for endoscope or endoscopic camera with two inlets and one outlet.
Figure 5B:
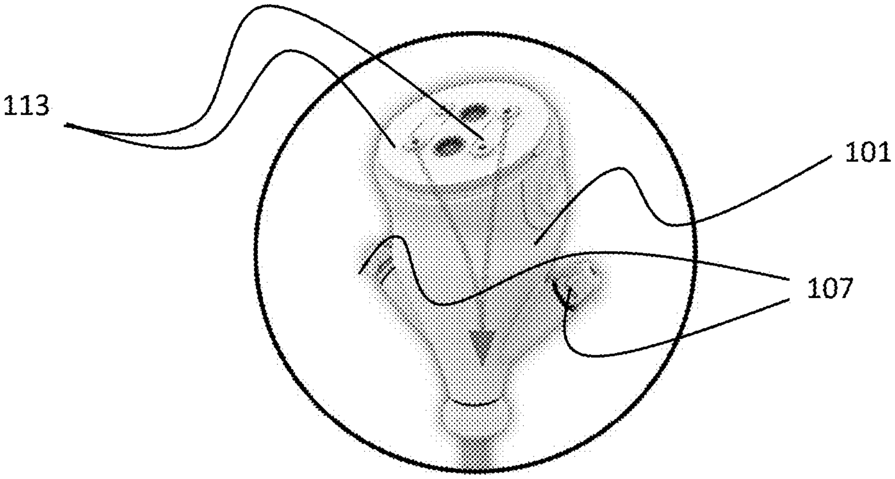
FIG. 5B shows the channel for each robotic manipulator with two inlets and one outlet.
Figure 5C:
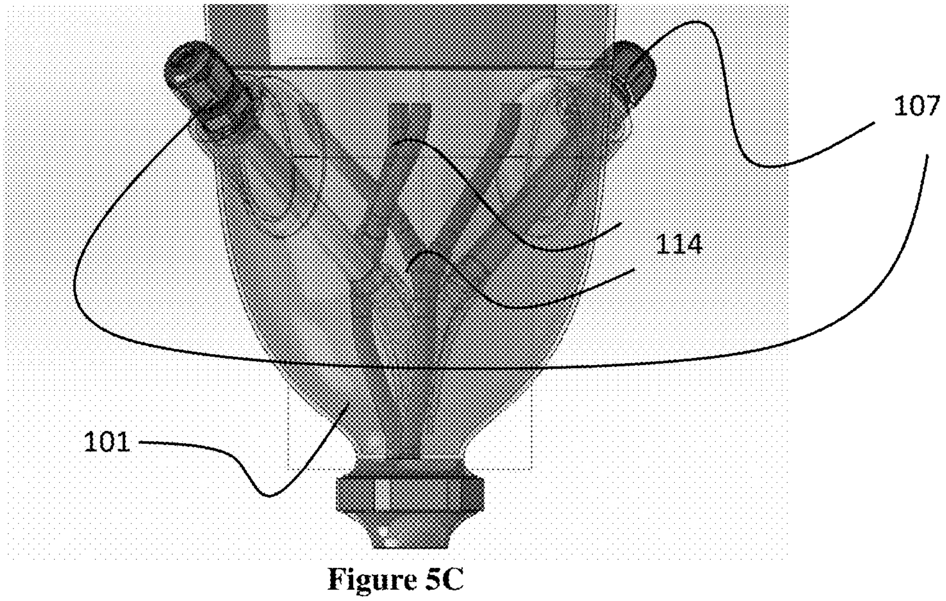
FIG. 5C shows the internal view of the channel for endoscope or endoscopic camera and robotic manipulators.
Figure 6:
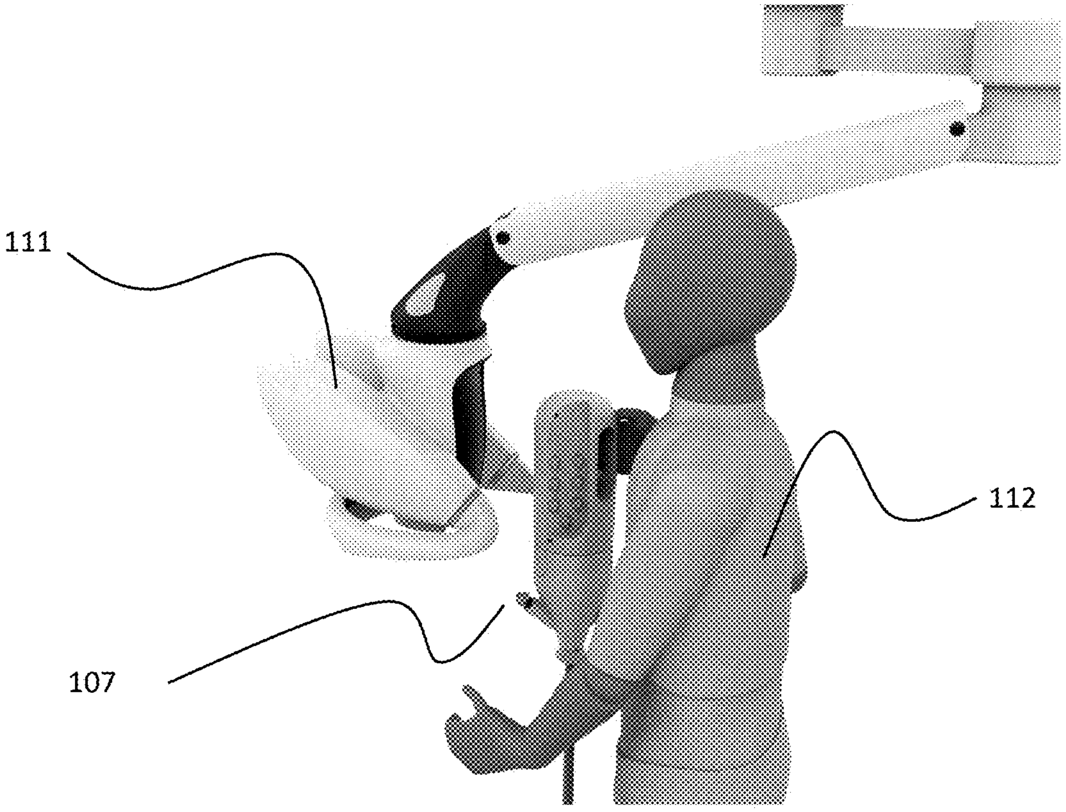
FIG. 6 shows the typical moment of the all-in-one adaptor is being detaching from the robotic carrier system.
Figure 7:
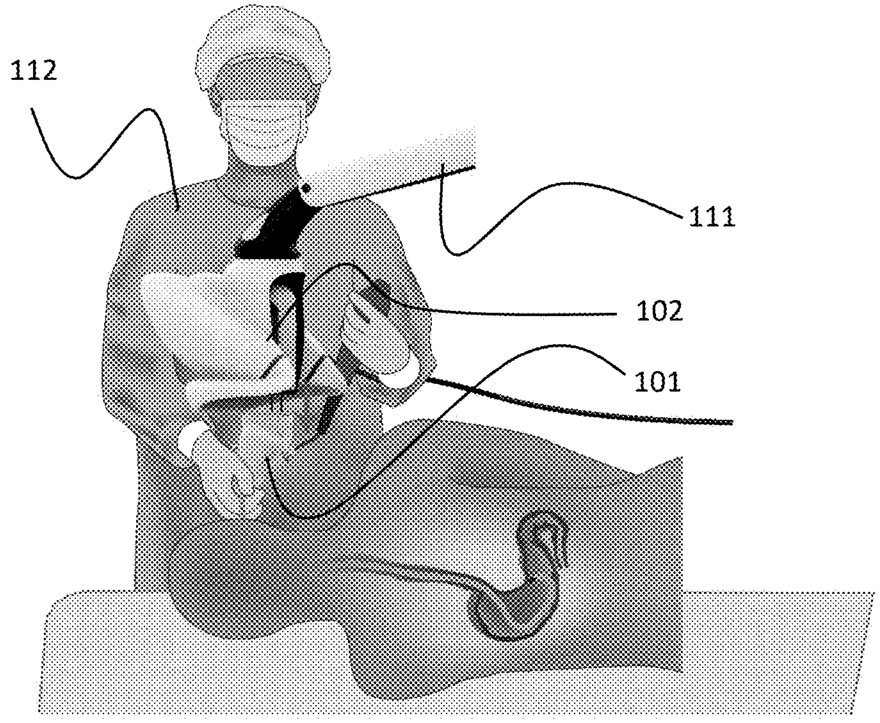
FIG. 7 shows the typical moment of the bowl of the all-in-one adaptor with the carrier system attached to the endoscopic overtube which is positioned within the patient.
Figure 8:
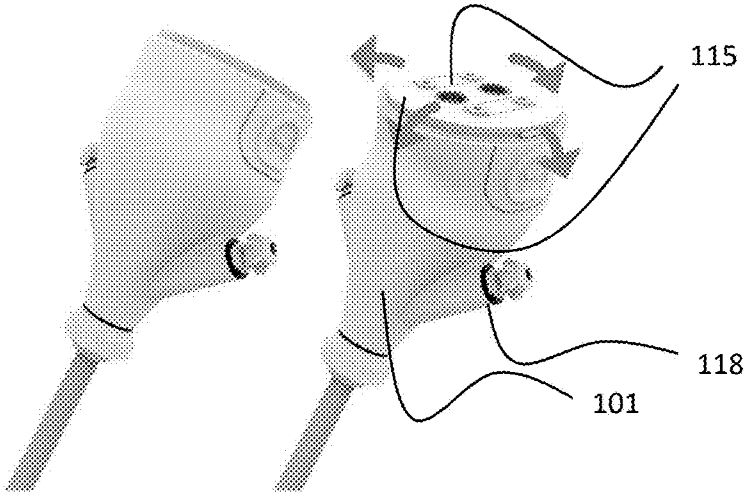
FIG. 8 shows the angle tilting ability of the proximal surface of the endoscopic overtube.
Figure 9A:
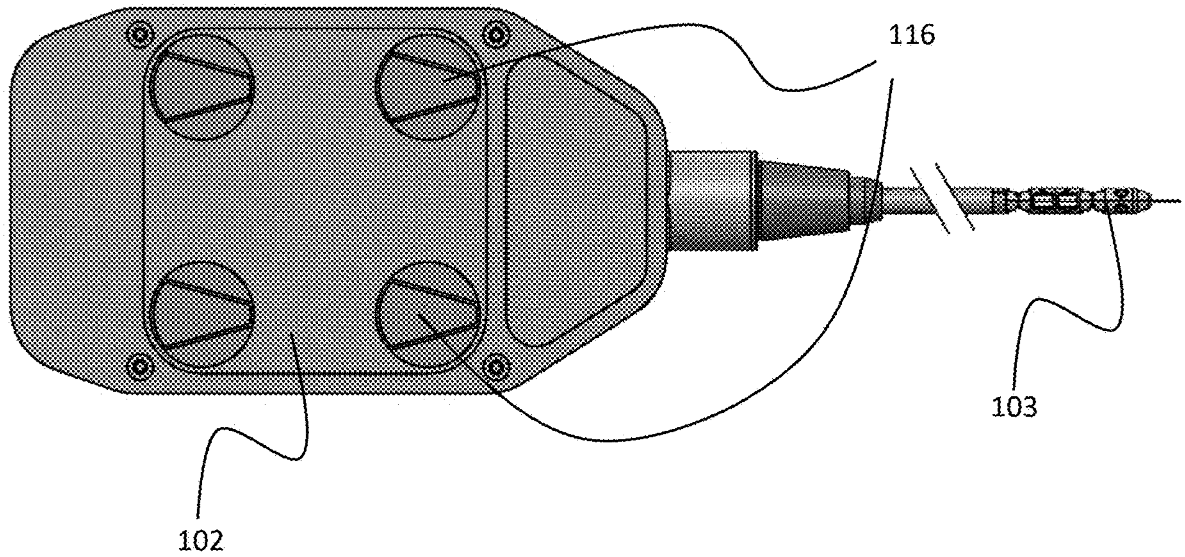
FIGS. 9A and 9B show the various embodiments of the bowl.
Figure 9B:
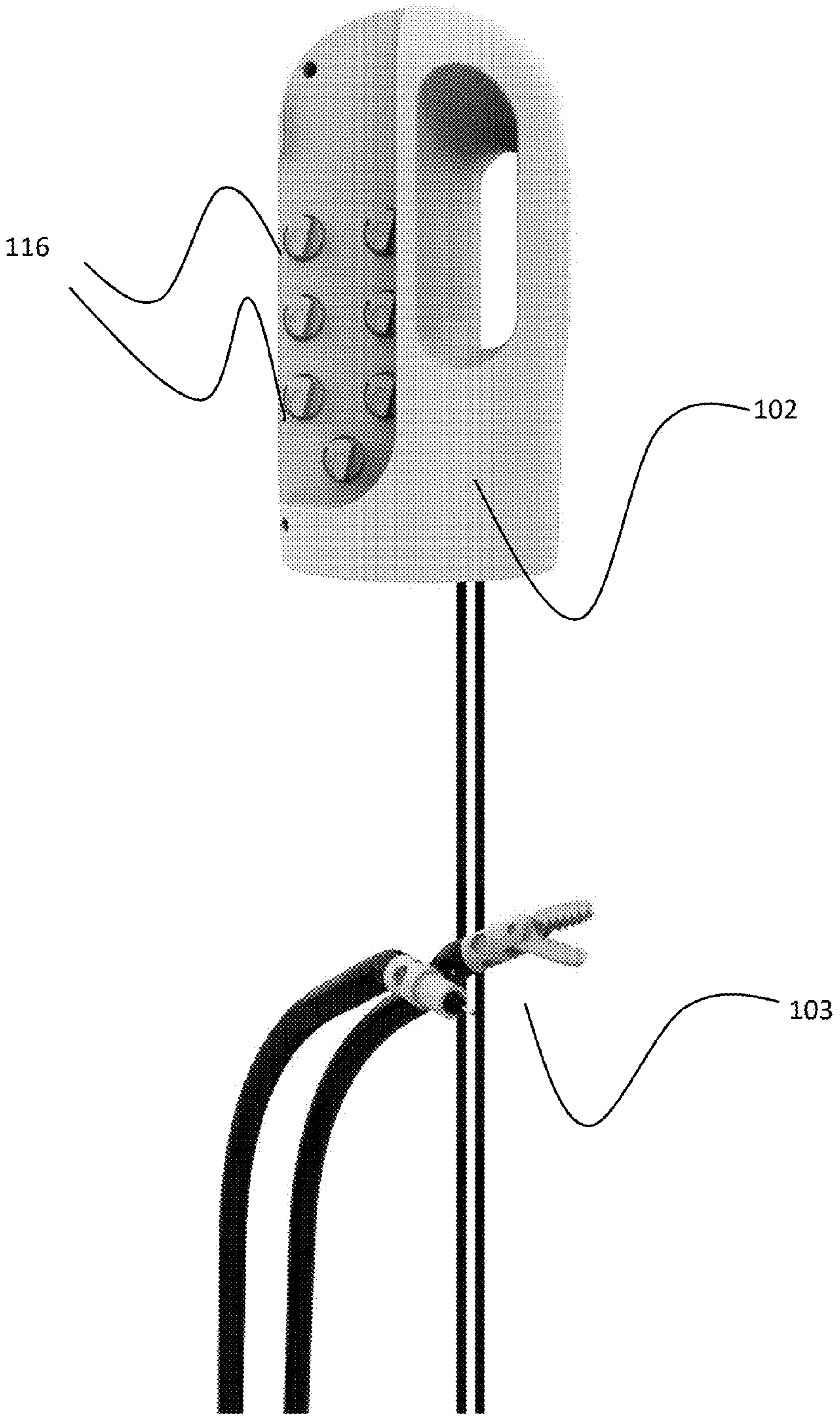
Figure 10:
FIG. 10 shows the typical holding position of the bowl and the endoscopic overtube by the operator.

Described herein is the structure and method of an all-in-one adaptor for deploying flexible robotic manipulator into human body for performing surgery operation. The all-in-one adaptor includes a bowl and an endoscopic overtube for accepting different tools: endoscope, endoscopic camera or flexible manipulator, for solving the difficulties in the current situation using conventional endoscopic devices.

In one embodiment, the present invention provides a detachable all-in-one adaptor for flexible robotic manipulator use in the surgical robotic platform. The system and method of the bowl and the endoscopic overtube in the all-in-one adaptor for flexible robotic manipulator using in the surgical robotic platform are disclosed. The component of the all-in-one adaptor includes an endoscopic overtube with internal channels for instruments, including but not limited to flexible robotic manipulator, endoscope, or endoscopic camera; a quick release and alignment mechanism to attach the endoscopic overtube to the bowl(s); a quick release and alignment mechanism to attach the bowl and the all-in-one adaptor to a docking of a surgical robotic platform. All the controllable actions of the robotic manipulators are controlled through the wired connection between the knots and the corresponding location of the robotic manipulator to maintain a stable and robust performance of the flexible robotic manipulator. An internal channel in the endoscopic overtube may be reserved for using endoscope or an endoscopic camera. One or more than one entrances are allowed to be used for the same endoscope or endoscopic camera to accommodate different situations.

In one embodiment, the present invention provides a carrier system for deploying flexible robotic manipulator of the surgical robotic platform into human body. It is designed to perform minimally invasive or non-invasive surgery with flexible robotic manipulators. The carrier system acts as a sheath for effective force transmission for operation. It is designed to ease the adapting of the robotic manipulator and to reach the designated operation area. An endoscope or endoscopic camera may be inserted in the carrier system to the distal end to provide vision. While when the endoscope or endoscopic camera is inserted, the carrier system's yaw and pitch navigation can be driven by the endoscope. The carrier system is operably coupled with the system of flexible robotic manipulator. To deploy the continuum robot into the human body, the robot manipulator can be either coupled or decoupled with the carrier system during deployment.

This invention provides a structure of the device for deploying flexible robotic manipulator in the surgical operation. In one embodiment, said structure comprises: A first member which is an endoscopic overtube with multiple internal channels for deploying endoscope, endoscopic camera, flexible robotic manipulator, or any endoscopic surgical tools; A second member which is a bowl embedded with flexible robotic manipulators with the quick release and alignment interface to assemble with the endoscopic overtube to become the all-in-one adaptor; A third member which is a carrier system for carrying the all-in-one adaptor during the surgical procedure in various positions and orientation, to allow the flexible manipulators can be located into the target location inside the human body correctly.

In one embodiment, the endoscopic overtube consists of a flexible tubing and a proximal surface with freedom of movement for attaching to the bowl.

In one embodiment, the bowl has two connection interfaces between the endoscopic overtube and between the carrier system for providing actuating force to the wire controlled flexible robotic manipulator from the carrier system.

In one embodiment, the carrier system can be constructed in different forms with the same purpose of usages, which it can be a tailor-made multi-degree-of-freedom robotic arm, commercially available robotic arm and ceiling arm.

In one embodiment, the bending of the distal tip of the flexible tube can be driven by the bending of the endoscope or endoscopic camera.

In one embodiment, more than one inlet is available of the channel for the endoscope or endoscopic camera, at which there is a Y-shaped inter-changed tube between the inlets and the single outlet channels.

In one embodiment, more than one inlet is available of the channel for each flexible robotic manipulator, at which there is a Y-shaped inter-changed tube between the inlets and the single outlet channels.

In one embodiment, the structure of this invention provide the opportunity for the user to switch between different inlets of that channel for additional freedoms of usage in different orientation of the endoscopic overtube.

In one embodiment, the structure can be operated independently at which the user can deploy the endoscopic overtube with the endoscope or endoscopic camera into human body.

In one embodiment, each of the inlet for the endoscope or endoscopic has a locking mechanism to reduce the diameter of the inlet for fixing the endoscope or endoscopic camera in place.

In one embodiment, the bowl embedded one or more flexible robotic manipulators which can be controlled by actuation wire.

In one embodiment, the flexible robotic manipulators are controlled through the connection of wire between the knot on the bowl and the wire constructed inside the flexible robotic manipulators.

In one embodiment, the bowl has a quick release and alignment interface with the endoscopic overtube at which the endoscopic overtube can be attached in every 90 degrees.

In one embodiment, the bowl has a quick release and alignment interface with the carrier system at which the actuation motion for the flexible robotic manipulators can be transfer from the motors inside the carrier system.

In one embodiment, the bowl is attached to the endoscopic tube after the endoscopic tube is positioned in place with the carrier system.

In one embodiment, the carrier system can be manipulated by human to control the position and the orientation of the distal end of the carrier system.

In one embodiment, the carrier system can be attached to the endoscopic overtube in different positions and orientations with the bowl, at which the endoscopic overtube is positioned in place by the user.

In one embodiment, the carrier system is in multi-degree-of-freedom robotic arm form can be installed on a mobile station for convenience delivery from different locations.

In one embodiment, the carrier system is in ceiling arm form can be installed in a well-established operation theater for minimizing the space occupied by the system.

In one embodiment, the carrier system is locked in place unless the user commands to unlock for changing position or orientation.

In one embodiment, the carrier system is locked in place unless the user commands to unlock for changing position or orientation.

This invention provides an adaptor for use with one or more robotic manipulators. In one embodiment, said adaptor comprises: a) a bowl (101) for attachment to a carrier system; b) an overtube (102) connected to said bowl (101), comprising at least one channel for insertion of said one or more robotic manipulators; c) a plurality of controls (118), each control (118) is adapted to control diameter of one of said at least one channel; wherein said at least one channel comprises two or more inlets (107) converging into a same channel; and each of said two or more inlets (107) is positioned on opposite sides on said bowl (101) or overtube (102).

In one embodiment, said overtube (102) is detachable from said bowl (101).

In one embodiment, said one or more robotic manipulators (103) is selected from the group consisting of a dissector (104) and a lifter (105).

In one embodiment, said one or more robotic manipulators (103) is a wire controlled flexible manipulator.

In one embodiment, said at least one channel comprises a channel for insertion of one or more selected from the group consisting of an endoscope, endoscopic camera (106) and an endoscopic surgical tool.

In one embodiment, said adaptor further comprises one or more bowls (101).

In one embodiment, said carrier system is selected from the group consisting of a tailor made multi degree of freedom robotic arm (108), commercially available certificated robotic arm (108) and ceiling movable robotic arm (111).

In one embodiment, said two or more inlets (107) converges into a same channel in a Y-shaped configuration (114).

In one embodiment, said overtube (102) comprises a tiltable surface for connection with said bowl (101).

In one embodiment, said bowl (101) comprises a shape adapted to connect with said carrier system.

In one embodiment, said adaptor further comprises a quick release and alignment interface for attachment between said bowl (101) and said overtube (102).

In one embodiment, said adaptor further comprises a quick release and alignment interface for attachment between said bowl (101) and said carrier system.

In one embodiment, said overtube (102) is a flexible tubing comprising a distal tip that is actuated by said one or more robotic manipulators (103).

In one embodiment, at least one of said controls (118) is a knob.

In one embodiment, said carrier system attached to said bowl (101) provides force for actuation of said one or more robotic manipulators (103).

This invention also provides a method for using the adaptor of this invention for surgery. In one embodiment, said adaptor of this invention comprises an overtube (102) is detachable from the bowl (101), said method comprises the steps of: a) positioning said overtube (102) at a target location; b) inserting an endoscope or endoscopic camera (106) into one of said at least one channel from one of said two or more inlets (107); c) attaching said bowl (101) to a carrier system; and d) connecting said bowl (101) to said overtube (102).

In one embodiment, said step (d) comprises manipulating said bowl (101) with said carrier system.

In one embodiment, said step (d) comprises tilting a proximal surface of said overtube (102) to connect with said bowl (101).

In one embodiment, said step (c) comprises attaching said bowl (101) to said carrier system at a quick release and alignment interface adapted for transfer of force from said carrier system to said one or more robotic manipulators (103).

In one embodiment, said method further comprises retracting said endoscope or endoscopic camera (106) after step (d).

This invention provides an all-in-one adaptor 100 for robotic manipulator(s) 103 using in the surgical robotic platform. In one embodiment, said the system includes a detachable and flexible endoscopic overtube 102 and bowl(s) 101 assembled with robotic manipulator(s) 103.

The endoscopic overtube 102 can be detached from the bowl 101, and which there is a quick release and alignment mechanism between them.

The bowl 101 can be assembled with one or more than one robotic manipulator(s) 103.

The robotic manipulator(s) 103 includes but not limited to a dissector 104 with tissue dissection ability and lifter 105 with tissue retraction ability.

Typically, three or more channels are available in the endoscopic overtube for providing at least one channel for endoscope or endoscopic camera 106.

There is more than one inlet 107 in the endoscopic overtube for the endoscope or endoscopic camera 106 for adapting different scenarios.

In one embodiment, there is more than one bowl 101 in the whole system.

For different situations or installation requirements in different operation theater, the all-in-one adaptor 100 can be installed or attached to different carrier system 108, 109, 111.

In one embodiment, the all-in-one adaptor is attached to a tailor-made multi-degree-of-freedom robotic arm 108.

In one embodiment, the all-in-one adaptor is attached to a commercially available medical certificated robotic arm 109.

The tailor-made multi-degree-of-freedom robotic arm 108 and the commercially available medical certificated robotic arm 109 are both installed on a movable platform for delivering surgical operation on the side of the patient bed, with at least one operator 110.

In one embodiment, the carrier system can be a ceiling movable arm 111, which is commonly used in operation theater.

The endoscopic overtube 102 is deployed before attaching to the bowl 101 for ensuring the distal tip of the overtube and the endoscope or the endoscopic camera 106 is located in the target location inside human body.

The bowl 101 is manipulated by the surgeon's 112 right hand, and the endoscope or endoscopic camera is manipulated by the surgeon's 112 left hand.

The surgeon 112 can deliver the endoscope or the endoscopic camera 106 from the inlet 107 on the bowl 101 to the distal end of the endoscopic overtube 102.

The endoscope or endoscopic camera 106 can be retracted from the endoscopic overtube 102 anytime for cleaning the lens.

The viewing angle of the endoscope or endoscopic camera 106 can be adjusted by rotating the endoscope or endoscopic camera 106 by surgeon's 112 left hand.

There are at least two inlets for endoscope or endoscopic camera 107 in the endoscopic overtube 102 while the outlet for that is the same in the distal end of the endoscopic overtube 102.

There are at least two inlets for each robotic manipulator 113 on the proximal surface of the endoscopic overtube 102, while the outlet for that is the same in the distal endo of the endoscopic overtube 102.

The mechanism for the multi-inlet single-outlet for the endoscope or endoscopic camera channel and robotic manipulator channel is that there is a Y-shaped inter-changed tube 114 inside the endoscopic overtube, such that the destination of each inlet is the same.

In one embodiment, there is no specifically allocated entrance for flexible robotic manipulators 103 or other tools. All entrances are feasible for different flexible robotic manipulators to go in. This could favor surgeons 112 who are left-handed or right-handed, also it allows more flexibility to handle complicated geometry of the surgical environment.

A knot 118 at the entrance of the channel of the endoscope or endoscopic camera is used to reduce the diameter of the channel. The knot 118 resist the endoscopic camera from translation inside the endoscopic overtube channel.

Once the endoscopic overtube 102 is positioned, the surgeon 112 may manipulate the carrier system 111 for attaching the bowl 102 on the endoscopic overtube 102, for deploying flexible robotic manipulator 103 into human body.

The endoscopic overtube 102 has a quick release and alignment mechanism 115 for the attachment on the bowl 101 to form an assembled all-in-one adaptor 100.

In one embodiment, the proximal surface of the endoscopic overtube 102 is tiltable relative to the rest of the endoscopic overtube 102. This tiltable function allow it to easily adapt with the bowl 101, which is already attached to the carrier system 111.

The flexible robotic manipulator 103 is controlled through wired connected using the connection interface 115 between the endoscopic overtube 102 and the bowl 101, as well as using the knot 116 between the bowl 101 and the carrier system 111.

The shape of the bowl 101 may be varied due to different configurations of the carrier system 111.

What is claimed is:

1. An adaptor for use with one or more robotic manipulators (103), comprising a. a bowl (101) for attachment to a carrier system;

b. an overtube (102) connected to said bowl (101), comprising at least one channel for insertion of said one or more robotic manipulators;

c. a plurality of controls (118), each control (118) is adapted to control diameter of one of said at least one channel;

wherein said at least one channel comprises two or more inlets (107) converging into a same channel; and each of said two or more inlets (107) is positioned on opposite sides on said bowl (101) or overtube (102).

2. The adaptor of claim 1, wherein said overtube (102) is detachable from said bowl (101).

3. The adaptor of claim 1, wherein said one or more robotic manipulators (103) is selected from the group consisting of a dissector (104) and a lifter (105).

4. The adaptor of claim 1, wherein said one or more robotic manipulators (103) is a wire controlled flexible manipulator.

5. The adaptor of claim 1, wherein said at least one channel comprises a channel for insertion of one or more selected from the group consisting of an endoscope, endoscopic camera (106) and an endoscopic surgical tool.

6. The adaptor of claim 1, further comprising one or more bowls (101).

7. The adaptor of claim 1, wherein said carrier system is selected from the group consisting of a tailor made multi degree of freedom robotic arm (108), commercially available certificated robotic arm (108) and ceiling movable robotic arm (111).

8. The adaptor of claim 1, wherein said two or more inlets (107) converge into a same channel in a Y-shaped configuration (114).

9. The adaptor of claim 1, wherein said overtube (102) comprises a tiltable surface for connection with said bowl (101).

10. The adaptor of claim 1, wherein said bowl (101) comprises a shape adapted to connect with said carrier system.

11. The adaptor of claim 1, further comprising a quick release and alignment interface for attachment between said bowl (101) and said overtube (102).

12. The adaptor of claim 1, further comprising a quick release and alignment interface for attachment between said bowl (101) and said carrier system.

13. The adaptor of claim 1, wherein said overtube (102) is a flexible tubing comprising a distal tip that is actuated by said one or more robotic manipulators (103).

14. The adaptor of claim 1, wherein at least one of said controls (118) is a knob.

15. The adaptor of claim 1, wherein said carrier system attached to said bowl (101) provides force for actuation of said one or more robotic manipulators (103).

16. A method for using said adaptor of claim 1 for surgery, said overtube (102) is detachable from said bowl (101), comprising the steps of:

a. positioning said overtube (102) at a target location;

b. inserting an endoscope or endoscopic camera (106) into one of said at least one channel from one of said two or more inlets (107);

c. attaching said bowl (101) to a carrier system; and d. connecting said bowl (101) to said overtube (102).

17. The method of claim 16, wherein said step (d) comprises manipulating said bowl (101) with said carrier system.

18. The method of claim 16, wherein said step (d) comprises tilting a proximal surface of said overtube (102) to connect with said bowl (101).

19. The method of claim 16, wherein said step (c) comprises attaching said bowl (101) to said carrier system at a quick release and alignment interface adapted for transfer of force from said carrier system to said one or more robotic manipulators (103).

20. The method of claim 16, further comprises retracting said endoscope or endoscopic camera (106) after step (d).

* * * * *